United States Patent [19]
Silvetti, Sr.

[11] Patent Number: 6,046,178
[45] Date of Patent: *Apr. 4, 2000

[54] METHOD AND COMPOUND FOR TREATING WOUNDS WITH STARCH HYDROLYSATE MEDICATION

[75] Inventor: Anthony N. Silvetti, Sr., River Forest, Ill.

[73] Assignee: DeRoyal Industries, Inc., Powell, Tenn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/844,240

[22] Filed: Apr. 18, 1997

[51] Int. Cl.⁷ ..................................... A61K 33/26
[52] U.S. Cl. ............. 514/60; 514/58; 514/561; 514/564; 514/928; 4245/630; 4245/642; 4245/DIG. 13
[58] Field of Search ..................... 424/630, 642, 424/DIG. 13; 514/60, 58, 561, 564, 928

[56] References Cited

U.S. PATENT DOCUMENTS

| | | | |
|---|---|---|---|
| 3,812,252 | 5/1974 | Silvetti | 424/180 |
| 4,414,202 | 11/1983 | Silvetti | 424/147 |
| 4,778,679 | 10/1988 | Silvetti | 424/147 |
| 4,847,083 | 7/1989 | Clark . | |
| 4,889,844 | 12/1989 | Silvetti, Sr. et al. | 514/60 |
| 5,126,141 | 6/1992 | Henry . | |
| 5,177,065 | 1/1993 | Silvetti, Sr. et al. | 514/53 |
| 5,415,865 | 5/1995 | Soderberg et al. . | |

*Primary Examiner*—Rebecca Cook
*Attorney, Agent, or Firm*—Chapman & Cutler

[57] ABSTRACT

A medication and method for treating wounds by contacting the wound, for a sufficient period of time, with a therapeutically effective amount of a starch hydrolysate composition including trace elements, to beneficiate the wound healing processes. A possible starch hydrolysate is maltodextrin and possible trace elements include, at least copper and zinc. The composition may also contain ascorbic acid as well as antibacterial and nutritive agents to promote formation and growth of granulation tissue.

30 Claims, No Drawings

METHOD AND COMPOUND FOR TREATING WOUNDS WITH STARCH HYDROLYSATE MEDICATION

FIELD OF THE INVENTION

The present invention relates to methods and compositions for treating wound with a starch hydrolysate medication. More specifically, it relates to the addition of trace metals, such as copper and/or zinc to the starch hydrolysate medication, to beneficiate wound healing process.

BACKGROUND OF THE INVENTION

During the period following development or infliction of serious physical damage to the skin, by way of for example, severe burns, wounds, pressure ulcers, and the like, the injured area is extremely unstable physiologically. Following such injury or trauma, the normal physiological processes of the area in question may be severely compromised. Disruption in the normal pattern of skin growth, blood flow, and immunity may all be impaired to some extent by the trauma to the region. The health care provider treating such damaged tissue must therefore be able to control and eventually reverse these undesirable effects, while at the same time stimulating the processes that are necessary to achieve healing of the area.

Because of the variety of different systems which may be adversely affected by such injury, it is difficult to find a single agent which will be effective in controlling the various sources of the problems. For example, one of the most severe difficulties encountered is the immediate colonization of the wound by a variety of different types of microbial species. Common invaders of a wound site are known pathogens such as *Staphylococcus aureus,* as well as a number of opportunistic pathogens, such as *Escherichia coli* or *Pseudomonas aeruginosa.* Various yeasts, particularly *Candida albicans,* may also be found at the wound. Although a number of antimicrobial agents for topical application are known, none has proven to be without some serious disadvantage. For example, silver sulfadiazine, the current antibacterial agent of choice, is effective against gram-positive and gram-negative bacteria but many resistant strains have developed in the course of its use, particularly in the genus, Pseudomonas. Similarly, the commonly used 10% pvp iodine, although effective against both gram-positive and gram-negative bacteria, can be quite painful to the patient upon application, kills white cells in the wound, specifically polymorphonuclear cells, lymphocytes, monocytes, macrophages, fibroblasts, endothelial cells and keratinocytes and may cause sensitization of an area already severely traumatized. Other known antibacterial agents may be hampered in their use by low diffusibility of the composition, or a range of activity that covers relatively few types of microbes. Expense, as with substances such as the various silver salts, is also a factor to be considered.

Related to the invasion by microbes of the wound site is the generally decreased circulation which is also observed in many cases. For example, in decubitus or stasis ulcers, a cessation of blood flow may develop gradually, whereas an acute cessation of flow may occur in thermo-radiation and chemical burns. In either case the decrease in the rate of blood flow means a corresponding decrease in the provision to the cells of nutrients and oxygen. Thus deprivation in turn leads to necrosis of tissue in the poorly supplied region, which will be followed by the invasion of the unwanted bacteria and fungi. In order for healing to proceed, the damaged area must not only be rid of any lingering microbial infection, but also must have a restored blood flow, which will provide sufficient nutrient and oxygen supply to support regeneration of the wounded region. In the ideal situation, the increased blood flow should also be accompanied by the formation of healthy granulation tissue. The latter is a layer of highly vascularized tissue, containing numerous fibroblasts and collagen and ground substance, which supports the normal wound healing processes of recollagenation and re-epithelialization.

Another very critical aspect of the wound healing process is the initiation of wound closure. This is generally a two-stage process, comprising contraction and epidermal migration. Contraction is the process of bulk skin movement from the edges of the wound, while migration is the separation and movement of activated epidermal cells over the surface of the wound. Because contraction itself may lead to some scarring, it is preferable to be able to speed healing in a manner which will increase the process of epidermal migration. The process of migration is characterized by a stimulation of mitosis in the epidermal cells, accompanied by movement across the wound site. The extent to which epidermal migration, and thus wound closure, can be promoted will also in some cases determine whether or not additional skin grafting is required to complete the healing of the wound.

It is thus evident that a large number of different factors must be controlled and/or stimulated in order to achieve thorough regeneration of the damaged tissue. Since the processes involved, and the mechanisms controlling them, are so diverse, it has proven difficult to pinpoint a single treatment composition or method which is capable of aiding and promoting most or all of the required processes simultaneously. As noted above with respect to the various antibacterial agents available, the majority of wound healing compositions and delivery systems presently available suffer from one or another deficiencies, whether it be in complexity of application, insufficient ability to control precise application of the dressing, irritation caused to the patient, or expense. For example, with powder compositions, contact with the wound is limited to where the powder falls on the wound and even with careful application, more powder than necessary can be used and it is difficult to apply the powder to all areas of the wound. Use of a gel medium of selected viscosity is more effective at accelerating mitotic division of the epidermal cells, fibroblasts, and endothelial cells of the connective tissue because the gel, having fluid properties, flows into all areas of the wound and therefore increases delivery of wound-healing agents to the wound more directly.

BRIEF DESCRIPTION OF THE INVENTION

The present invention relates to a composition comprising a therapeutically effective amount of a pharmaceutically acceptable starch hydrolysate in powder form with trace amounts of copper, zinc or other metal. Sterile water may be added to form an emulsion of desired viscosity with a pharmaceutically acceptable gelatinization agent. In its preferred embodiment, the present invention relates to a composition comprising an effective amount of a starch hydrolysate and trace metals, and preferably to such a composition comprising glycerin and a starch hydrolysate having a dextrose equivalent of between 13 and 17. The viscosity of the composition is preferably in the range of 31,000 to 35,000 centipoise in order to facilitate exposure of dermatological agents added to improve healing and to facilitate contact to all areas of the wound including those that may be partially covered.

The present invention also provides a method of treating wounds which comprises contacting the wound with the compositions described above for a period of time sufficient to initiate wound healing.

DESCRIPTION OF THE INVENTION

This invention relates to the treatment of skin wounds such as second and third degree burns, stasis ulcers, ischemic ulcers, trophic lesions, decubitus ulcers, severe cuts, deep punctures, abrasions, full thickness skin losses, skin undermining and deep skin tunnels.

The aforementioned skin wounds are characterized by open wounds or gaps in the skin tissue. As the healing process progresses these open wounds are gradually filled in by new cells which appear across the surface of the open wound so that when the healing process is complete, new skin tissue covers the former open area of the wound. Such cells are termed granulation tissue cells and the healing mechanism is a granulation cell formation process. These granulation cells and the blood capillaries supplying them are, however, very fragile and rupture easily. Heretofore, conventional dry gauze dressings have been used widely on such burns or exudative lesions. When dry gauze is removed, as for example when it is changed, the cells and capillaries rupture; thus temporarily arresting the healing process. A dressing for burns and exudative lesions, therefore, should be capable of removal without disturbing the growth of the very fragile granulation tissue.

As a defense mechanism the body rushes edemic fluids to the area of these skin wounds and such wounds usually exude this edemic liquid. Consequently, vital body fluids are lost in the exudate. Heretofore, the conventional technique to prevent this loss of vital body fluids has been to attempt to seal off the exuding wound. This has been accomplished, for example, by applying to the wound a layer of petrolatum or other water immiscible hydrocarbon material. However, it has been found that the tissue under such a layer of petrolatum is often excessively soft, wet and macerated. This softened tissue causes difficulty in both autograft and homograft skin transplants. It also provides an environment that is conducive to the development of secondary infections. The wound, therefore, must be cleansed constantly. But cleansing necessitates removal and replacement of the dressing and, as described above, there is great danger of rupturing the very fragile granulation tissue cells and capillaries during this removal and replacement process.

Soft protein, polysaccharide and polymer films have been used instead of a petrolatum seal in the treatment of burns or exudative lesions, but encounter the same problem of the underlying tissues becoming excessively soft. In addition, these films collect exudate underneath and have a tendency to lift up and must then be removed and reapplied. This removal and replacement process again creates the possibility of rupturing the very fragile granulation cells and capillaries.

Powders containing starch have been used with many improvements over the protein films and petrolatum. However, with such powders an excessive amount of product must be applied to the wound to compensate for material falling outside the wound. Additionally, the powder, even with careful application, only contacts the areas of the wound where it lands. The powder does not reach areas of the wound, particularly along the edge, that may be covered with torn skin nor does the powder reach areas of the wound that have more depth than the surrounding wound surface. While dermatological agents that aid healing can be blended with a starch-based powder, they are not necessarily available to the entire wound surface because the powder lacks fluidity.

A method for the treatment of the aforementioned skin wounds should, therefore, permit the use of a dressing which is as close as functionally possible to a natural wound scab, be permeable to exudate but not to proteinaceous material, be water vapor permeable, be flexible and not lift up, and inhibit the start or spread of secondary infections by reducing the bacteria count in and around the treated wound. In the treatment of second and third degree burns, the dressing employed should be similar to a skin autograft in that it affords a natural protective covering which promotes healing, and yet it should, like a homograft, be easily sloughed off by the body when the healing process is completed.

DETAILED DESCRIPTION OF THE INVENTION

The therapeutic use of starch hydrolysate as a film-forming agent has been described in U.S. Pat. Nos. 3,812,252 and 4,414,202, the teachings of which are incorporated herein by reference. In brief, starch hydrolysate has been shown to be an exceptionally effective treatment for burns, ulcers, lesions, and other skin defects such as wound dehiscences. The starch hydrolysate mixes with the proteins in the wound fluid and forms a film which ultimately adheres to underlying tissue and which is semipermeable to air and fluid. It thus provides a covering which reduces plasma and fluid loss, while also preventing invasion and proliferation of pathogenic microbes. Another outstanding property of the starch hydrolysate is its antimicrobial effects, such as bacteriostatic and bacteriocidal effects. The effects observed with use of starch hydrolysate are far superior to results seen with use of traditional wound-treating methods and the like.

When a pharmaceutically acceptable starch hydrolysate is blended with a sufficient amount of sterile water and a gelatinization agent to form a gel, the effect is enhanced wound healing. The result is an improvement in effectiveness over dry powder compositions containing starch hydrolysate. The gel composition has all the benefits of a powder and provides for more efficient and more thorough wound healing. The gel, having a viscosity in the desired range, provides a better result in application of the starch hydrolysate to the wound. There is better product control with a gel and the fluid flow of the gel brings the wound healing benefits of the starch hydrolysate to areas of the wound a powder may not reach.

Those skilled in the art are aware that starch hydrolysate is a generic term of a mixture of carbohydrates most commonly classified according to their dextrose equivalent. The starch hydrolysate of the present invention is one which has a dextrose equivalent of no more than 60, and preferably no more than 30. More preferably, the dextrose equivalent of the starch hydrolysate of the present invention is between about 7 and 20.

Still more preferably, the dextrose equivalent of the starch hydrolysate is between about 7.5 and 30. Most preferably, the starch hydrolysate of the present invention has a dextrose equivalent in the range of between about 13 and 17. Those skilled in the art are aware that starch hydrolysates having a dextrose equivalent in this latter most preferred range are more specifically called maltodextrins. It will also be understood that "pharmaceutically acceptable" means purified and sterilized. While any of the known methods, including dry heat, filtration, or irradiation may be used for the sterilization, the preferred method of the present invention is Gamma Radiation.

Maltodextrins are produced from starch by hydrolysis. Starch is a polymer of anhydro-D-glucose units. Hydrolysis of starch produces a mixture of polymers of various molecular weights ranging from 200 glucose units or more down to maltose (2 glucose units) and D-glucose itself. Because of their nature the accepted way to describe the polymers formed by hydrolysis of starch is by their D.E. value, which is an expression of the average extent of hydrolysis.

The dressing also has been found to act as a semipermeable membrane which allows edemic liquids to pass through it while proteinanceous materials are retained within the body. The exudate is clean and relatively free of proteinaceous materials. It, therefore, does not support biological oxidation to the same extent as exudate containing proteinaceous fluids is minimized while at the same time excessive build up of edemic liquids is also minimized. The possibility of the patient going into shock is, therefore, greatly reduced. It has been found that when applied to an exudative skin wound, this dressing greatly reduced the bacterial count of an infected wound, and inhibits infection of an uninfected wound. Thus, the possibility of a secondary infection occurring is greatly reduced. Toward this end the sterile, purified starch hydrolysate particulate material having a D.E. less than about 35 may be admixed with any of the antibacterial agents known to the art to be effective in the prevention or treatment of secondary infections, e.g., iodine, penicillin, nitrofurances and the sulfa drugs such as silver sulfadiazine. In addition, proteolytic enzymes known by the art to be effective in promoting healing may also be admixed with this particulate material. Furthermore, nutritive agents, such as the amino acids, cystine and cysteine, and vitamins, such as ascorbic acid (Vitamin C), may also be admixed or applied along with this particulate material to promote the formation and growth of healthy granulation tissue.

The sterile, purified starch hydrolysate material having a D.E. of less than about 35 can be applied as a particulate material such as a powder, or as a viscous material such as a gel, paste, dispersion, solution or syrup. Such viscous starch hydrolysate can be made by adding the starch hydrolysate to a non-toxic, polar liquid vehicle or carrier such as water, glycerin, glycols or polyols.

The low D.E., sterile, purified starch hydrolysate material may be applied directly to the wound or it may, to facilitate handling and storing, be applied to a bibulous backing, as for example a sterile gauze pad, and the bibulous backing then applied to the wound so that the starch hydrolysate material comes into contact with the skin wound.

As has been previously mentioned, when the low D.E. starch hydrolysate material is applied to an exudative wound a film resembling a natural wound scab is formed. To promote the formation of this protective film, the formation of the protective film, the treated wound should not be tightly bandaged, but should only be loosely covered so that the wound can "breathe." It has been found that application of this material serves also to reduce the pain that is usually associated with burns, ulcers, and the like. This film also has the aforementioned properties of being flexible, semipermeable, soluble in water and antiseptic to the bacteria of the wound.

Starch hydrolysate materials for use in practicing the present invention are those having a D.E. of less than about 35, and preferably from about 5 to about 25. These materials are produced from starch by hydrolysis.

Starch is a polymer of anhydro-D-glucose units. Hydrolysis of starch produces a mixture of polymers of various molecular weights ranging from 200 glucose units or more down to maltose (3 glucose units) and D-glucose itself. Because of their nature the accepted way to describe the polymers formed by hydrolysis of starch is by their D.E. value, which is an expression of the average extent of hydrolysis.

Low D.E. products suitable for use in the present invention may be made by subjecting gelatinized starch to the hydrolytic action of an acid or an enzyme or successive treatments with such agents. The hydrolysate so formed is then purified by conventional means such as by subjecting it to filtration, centrifugation, decantation or the like to separate and remove any water insoluble materials remaining after hydrolysis. This material, dissolved in water to the extent of 10 grams per 100 ml. will contain less than 0.1 percent insoluble material as determined by filtration and drying the residue to constant weight under vacuum at 100° C. If desired the hydrolysate material may be subjected to further purification steps known to the art such as carbon or clay treatment, dialysis, electrodialysis, osmosis, ion exclusion, ion exchange and the like. The starch hydrolysate material employed in practicing the invention may be prepared from starch by a number of specific methods.

Low D.E. products suitable for use in the present invention may be made by subjecting gelatinized starch to the hydrolytic action of an acid or an enzyme or by successive treatments with such agents. The hydrolysate so formed is then purified by conventional means such as by subjecting it to filtration, centrifugation, decantation or the like to separate and remove any water insoluble materials remaining after hydrolysis. The hydrolysate, dissolved in water to the extent of 10 grams per 100 ml, will contain less than 0.1 percent insoluble material as determined by filtration and drying the residue to constant weight under vacuum at 100° C. If desired, the hydrolysate material may be subjected to further purification steps known to the art such as carbon or clay treatment, dialysis, electrodialysis, osmosis, ion exclusion, ion exchange and the like.

In one method, a starch, such as waxy starch, is treated with a single enzyme application of bacterial alpha-amylase. More specifically, an aqueous slurry of a starch such as waxy starch having a solids content less than 50 percent is subjected to the hydrolytic action of bacterial alpha-amylase under suitable conditions to produce the starch hydrolysate material. This material is further specifically characterized as having the sum of the percentages (dry basis) of saccharides therein with a degree of polymerization of 1 to 6, divided by the D.E. to provide a ratio greater than about 2.0. This ratio is referred to as the "characteristic" or "descriptive" ratio. Those materials having a descriptive ratio less than about 2 are somewhat undesirable in that they exhibit less water solubility and also tend to form a haze in solution as compared to those products with a ratio of about 2 or greater.

Those skilled in the art are aware that starch hydrolysate is a generic term of a mixture of carbohydrates most commonly classified according to its dextrose equivalent. The starch hydrolysate of the present invention is one which has a dextrose equivalent of no more than 85, but preferably no more than 40. More preferably, the dextrose equivalent of the starch hydrolysate of the present invention is between about 5 and 40. Still more preferably, the dextrose equivalent of the starch hydrolysate is between about 7.5 and 30. Yet still more preferred is a starch hydrolysate having a dextrose equivalent in the range of between about 10 and 20. More preferably, the starch hydrolysate of the present invention has a dextrose equivalent in the range of between about 13 and 17. Those skilled in the art are aware that starch hydrolysates having a dextrose equivalent in this latter most preferred range are more specifically maltodextrins.

The action of the film-forming agent combined with monosaccharide may be further enhanced by the incorporation of small amounts of optional ingredients. The optional components generally do not constitute more than 5% of the total weight of the composition.

In the preferred embodiment, a principal additional component of the composition of the present invention is one which includes a pharmaceutically acceptable metal, such as copper or zinc, or a salt thereof. A pharmaceutically acceptable salt thereof promotes the formation and growth of healthy granulation tissue. Among the pharmaceutically acceptable salts contemplated for use in this invention include one or more pharmaceutically acceptable metal salts selected from the group consisting of iron, calcium, copper, magnesium, selenium, silver, manganese, zinc and mixtures thereof. The incorporation of one or more of these salts in the composition of the present invention beneficiates the process of its healing. It is emphasized that more than one of these salts may be included in the composition of the present invention. Among the other salts contemplated for use here are calcium ascorbate, calcium chloride, calcium iodate, calcium permanganate, calcium phosphate (mono-, di, and tribasic), calcium gluconate, zinc acetate, zinc carbonate, zinc chloride, zinc citrate, zinc iodate, zinc oxide, zinc permanganate, zinc proxide, zinc salicylate, zinc stearate, zinc sulfate, magnesium chloride, magnesium citrate, magnesium chloride, magnesium sulfate, manganese chloride and copper sulfate.

Another component may be included in the composition of the present invention. This component is one or more amino acids which also improve healing. In a preferred embodiment one or more, up to all, of the following amino acids may be provided in the composition of the present invention: isoleucine, leucine, lysine, methionine, phenylalanine, threonine, tryptophane, valine, tyrosine, alanine, arginine, glycine, proline, histidine, serine, asparagine, aspartic acid, cysteine, cystine, glutamine and glutamic acid. Of these, glycine, proline and lysine are particularly preferred.

It will be understood that, as used herein, the term "amino acid" refers to both the pure form and the hydrochloric acid salts of the amino acids. Thus, in preferred embodiments of the present invention wherein amino acid is employed, one, two or all three of the above preferred amino acids are included in the composition of this invention. In general, the amount of amino acid in the composition should not exceed 1%.

In a particularly preferred embodiment, the composition of the instant invention includes starch hydrolysate and a monosaccharide selected from the group consisting of d-fructose, d-glucose, and d-sorbose. More preferably, the composition of the present invention comprises a starch hydrolysate having a dextrose equivalent of not more than 40, and d-fructose. Preferably, the fructose comprises up to about 30% of the total weight of the composition.

Suitable starch hydrolysate materials may also be made via a number of other routes. For example, a mixture of starch and water having a solids content less than 50 percent may be first subjected to the hydrolytic action of a bacterial alpha-amylase. After an initial thinning by the enzyme, the resulting partial hydrolysate is heated to a temperature sufficient to solubilize any unsolubilized starch. Since this temperature also tends to inactivate the enzyme, it is then necessary to subject the solubilized partial hydrolysate to a second hydrolysis by treatment with more bacterial alpha-amylase to obtain the final starch hydrolysate.

A third method of making the preferred class of starch hydrolysate materials consists of hydrolyzing a mixture of starch and water by the action of acid to reach a D.E. of less than about 35. The partial hydrolysate is subsequently subjected to the action of bacterial alpha-amylase to obtain a starch hydrolysate having a D.E. between 5 and 25.

A particularly preferred product useful here has the following specifications: moisture content, 5% (five) maximum; 9–13 D.E.; pH of 4.5 to 5.5 when in aqueous solution at 10% (ten) solids; an average bulk density of 28–35 pounds per cubic foot and a descriptive ratio of about 2.

Any starch or starch like material may be used to prepare the starch hydrolysate material used in the invention. Suitable materials include cereal and tuber starches, such as corn, wheat, potato, tapioca, rice, sago and grain sorghum; waxy starches may also be used. Hydrolysis may be carried out by enzymes, acids or combinations of the two.

In a preferred embodiment, the starch hydrolysate used in the present invention is a pharmaceutically acceptable maltodextrin, such as the commercially available product sold under the brand name Maltrin M150. The weight percentage of maltodextrin in the wound healing composition should be in the range of 57 to 77% to form the continuous phase with the sterile water. Preferably, the weight percentage of maltodextrin would be between 65 and 69% of the composition.

In order to improve the wound healing process, the present invention relates to a composition in the form of a gel. A gel is defined as an emulsion in which the dispersed phase has combined with the continuous phase to produce a semi-solid material as a jelly. The gel characteristics of the present composition allow for a better result in application of the starch hydrolysate to the wound. The wound healing gel is formed by blending the starch hydrolysate with a sufficient amount of sterile water to form the continuous phase. A gelatinization agent is then mixed into the continuous phase so that it becomes the dispersed phase. The result is an emulsion in semi-solid form with the gelatinization agent acting as the dispersed phase and the starch hydrolysate and water acting as the continuous phase. The gel has a final viscosity in the range of 29,000 to 37,000 centipoise.

The gelatinization agent can be any compound capable of acting as the dispersed phase in a semi-solid emulsion. In its preferred embodiment, the present invention relates to a composition comprising the gelatinization agent, glycerin. The glycerin should be USP/FCC grade, for example, as the type that may be supplied by American International Chemical, Inc. The weight percentage, sufficient to act as the dispersed phase of the semi-solid emulsion, of glycerin in the wound healing composition should be in the range of 2 to 20%. Preferably, the weight percentage of glycerin is in the range of 9 to 11%.

A sufficient amount of sterile water is used to form a continuous phase consisting of the starch hydrolysate and the sterile water. The weight percentage of sterile water in the wound healing composition should be in the range of 11 to 31% to form the continuous phase. Preferably, the weight percentage of water would be between 21 and 23% of the composition.

The blending of maltodextrin, the preferred starch hydrolysate compound, with sterile water, to form a continuous phase, and then introduction of the preferred gelatinization agent, glycerin, to form an emulsion produces a gel having several advantages over dry powders as a wound-healing treatment. The primary benefits are more efficient delivery of dermatological agents having a wound-healing effect and more thorough application of those agents to the wound area.

These benefits are caused by the viscosity of the gel. The selected gel viscosity has fluid flow so that the composition moves and spreads into areas of the wound that are not exposed to the external application of other wound-healing compositions such as a powder. As a result, the gel can better penetrate areas along the edge of the wound where there may be layers of skin partially covering the wound. The fluid flow of the gel also more efficiently delivers wound-healing agents to all areas of the wound because a gel spreads and a powder is limited in its activity to the areas of the wound where it lands and adheres. The gel improves wound-healing by improving delivery of the agents that cause wound closure by enhancing mitotic division of the epidermal cells. Another benefit of the gel composition of the selected viscosity is better product control in application and a reduced amount of product used.

These benefits are provided by a gel emulsion having a viscosity in the range of 29,000 to 37,000 cp. The gel viscosity was selected to provide the above-described benefits. Not all semi-solid emulsions would provide these benefits. A higher viscosity gel would not adequately disperse the wound-healing agents and a lower viscosity gel would cause slip and a lack of adherence to the wound surface. The gel can be applied so that it only contacts the wound area and is not wasted on the surrounding skin surface as would happen during application of other compositions such as a powder. For example, powder that does not immediately adhere to the wound surface falls away from the wound area. With a gel, the entire quantity of gel applied to the wound remains in contact with the wound surface.

In its most preferred embodiment, the present invention of a gel composition with improved wound healing capability has the following composition: M-150 maltodextrin (66 to 68.25 weight %), Sterile Water (21 to 23 weight %), and Glycerin (9 to 11 weight %), with a final viscosity in the range of 31,000 to 35,000 centipoise.

In addition to the physical benefits of the gel composition, there is a cumulative effect in the prevention of bacterial and viral growth provided by the combination of maltodextrin and glycerin. Maltodextrin, by itself, is highly bacteriostatic. High concentrations of glycerin are known to be virucidal and possibly bacteriostatic. As a result, a gel composition containing both maltodextrin and glycerin has the cumulative capability of preventing the growth of both bacteria and viruses.

In another preferred embodiment, a principal additional component of the composition of the present invention is one which includes ascorbic acid or a pharmaceutically acceptable salt thereof. Those skilled in the art are aware that ascorbic acid or a pharmaceutically acceptable salt thereof promotes the formation and growth of healthy granulation tissue. Among the pharmaceutically acceptable ascorbate salts contemplated for use in this invention are sodium ascorbate, potassium ascorbate and calcium ascorbate. However, it is emphasized that the acid, ascorbic acid itself, is most preferred. When employed, the ascorbate component is preferably used in an amount of from about 0.1–5% of the total weight of the composition, and most preferably comprises about 1–3.5% of the composition.

In a preferred embodiment, another component of the composition of the present invention is a monosaccharide such as fructose. The benefits of using a monosaccharide in conjunction with a film-forming agent were disclosed in U.S. Pat. No. 4,889,844, the teaching of which is incorporated by reference. A mixture of a starch hydrolysate with fructose has several beneficial effects including hastening the process of revascularization of the wound, a greater level of activity in the development of granulation tissue, and acceleration of wound closure such that the need for a skin graft is reduced or eliminated. Fructose also has a synergistic effect with starch hydrolysate in the inhibition of microbial growth at the wound site. The weight percentage of fructose in the wound healing composition should be in the range of 0.25 to 3% of the composition. Preferably, the weight percentage of fructose would be between 1 and 2% of the composition.

The materials used in practicing the invention should, of course, be sterile. Sterilization may be accomplished by any of the known sterilization procedures.

For the purpose of illustrating the present invention but not of limiting the same there is set forth below an example of the novel wound-healing gel composition herein described.

EXAMPLE 1

Gel composition of the following components on a weight by weight (w/w) proportion:

| | |
|---|---|
| M-150 Maltodextrin | 67.15% |
| Sterile Water | 21.85% |
| Glycerin | 10.0% |
| Ascorbic Acid | 1.0% |
| Total | 100.0% |
| Viscosity | 32,835 cp |

As heretofore has been mentioned, in practicing the invention, purified starch hydrolysate material having a D.E. of less than about 35 is used as the film-forming agent, however, the preferred sterile, purified starch hydrolysate material has a D.E. of between about 5 and about 25. The starch hydrolysate is water soluble so that it easily forms a continuous phase with sterile water and so that the continuous phase is miscible with the dispersed phase consisting of the gelatinization agent. Additionally, the water soluble gel composition need not be mechanically removed from a wound; it can be washed away by flooding with water. When undermining or tunneling occurs in an exudative skin wound, this composition dissolves in the exudate. On the open portion of the wound, dressing with the gel composition forms a covering which is very similar to a natural wound scab. This covering has been found to be flexible so that some movement of the treated area is possible without causing the covering to lift up and away from the exudative wound.

The gel composition of the invention also has been found to act as a semi-permeable membrane which allows edemic liquids to pass through it while proteinaceous materials are retained within the body. The exudate is clean and relatively free of proteinaceous materials. It, therefore, does not support bacteriological proliferation to the same extent as exudate containing proteinaceous fluids. At the same time excessive build up of edemic liquids is also minimized. The possibility of the patient going into shock is, therefore, greatly reduced.

It has also been found that when applied to a skin wound, the gel reduces the bacterial count of an infected wound, and inhibits infection of an uninfected wound. Thus, the possibility of a secondary infection particularly in puncture wounds is greatly reduced. Toward this end the sterile, purified gel composition may be admixed with any of the antibacterial agents known to the art to be effective in the prevention or treatment of secondary infections, e.g., iodine, penicillin, nitrofuranes and the sulfa drugs such as silver sulfadiazine. In addition, proteolytic enzymes known by the art to be effective in promoting healing may also be admixed with the gel composition. Furthermore, nutritive agents and vitamins, such as ascorbic acid (Vitamin C), may also be admixed or applied along with the gel composition to promote the formation and growth of healthy granulation tissue.

Finally, yet another component may be included in the composition of the present invention. This component is one or more amino acids which also improve healing. In a preferred embodiment one or more, up to all, of the following amino acids may be provided in the composition of the present invention: isoleucine, leucine, lysine, methionine, phenylalanine, threonine, tryptophane, valine, tyrosine, alanine, arginine, glycine, proline, histidine, serine, asparagine, aspartic acid, cysteine, cystine, glutamine and glutamic acid. Of these, glycine, proline and lysine are particularly preferred.

It will be understood that, as used herein, the term "amino acid" refers to both the pure form and the hydrochloric acid salts of the amino acids. Thus, in preferred embodiments of the present invention wherein amino acid is employed, one, two or all three of the above preferred amino acids are included in the composition of this invention. In general, the amount of amino acid in the composition should not exceed 1%.

As has been previously mentioned, when the gel composition is applied as a dressing to an exudative wound, a film resembling a natural wound scab is formed. To promote the formation of this protective film, the only be wound should not be tightly bandaged, but should only be loosely covered so that the wound can "breathe." It has been found that application of the gel composition serves also to reduce the pain that is usually associated with burns, ulcers, and the like.

While the foregoing representative embodiments and details have been shown for the purpose of illustration and invention, it will be apparent to those skilled in the art that various changes and modifications may be made therein without departing from the spirit or the scope of the invention. It is intended that all such changes and modifications will be embraced within this invention, provided they fall within the appended claims.

What is claimed is:

1. A method of treating a wound in a patient, the method comprising contacting the wound, for a period of time sufficient to initiate wound healing, with a therapeutically effective amount of a gel composition, the gel comprising a continuous phase of starch hydrolysate, sterile water, and a dispersed phase of a gelatinization agent, and wherein the composition has a viscosity between 29,000 and 37,000 centipoise.

2. The method of claim 1, further comprising a trace amount of metal.

3. The method of claim 2, wherein said starch hydrolysate has a dextrose equivalent of not more than 30.

4. The method of claim 1, wherein said starch hydrolysate has a dextrose equivalent of not more than 30.

5. The method of claim 4, wherein said starch hydrolysate is a maltodextrin having a dextrose equivalent of between about 13 and about 17.

6. The method of claim 1, wherein said gelatinization agent is glycerin.

7. The method of claim 2, wherein the metal comprises copper or a pharmaceutically acceptable salt thereof.

8. The method of claim 2, wherein the metal comprises zinc or a pharmaceutically acceptable salt thereof.

9. The method of claim 1, wherein the composition further comprises an antibacterial agent and a nutritive agent, whereby to promote formation and growth of granulation tissue.

10. The method of claim 1, wherein the composition further comprises a monosaccharide, whereby to accelerate revascularization, development of granulation tissue, and wound closure.

11. The method of claim 1, wherein the composition further comprises one or more amino acids, whereby to improve healing.

12. A method of treating a wound in a patient, the method comprising the step of contacting said wound, for a period of time sufficient to initiate wound healing, with a therapeutically effective amount of a gel composition, the gel comprising a continuous phase of maltodextrin, sterile water, at least one metal, and a dispersed phase of glycerin, and the gel having a viscosity between 29,000 and 37,000 centipoise.

13. The method of claim 12, wherein the metal comprises copper or a pharmaceutically acceptable salt thereof.

14. The method of claim 12, wherein the metal comprises zinc or a pharmaceutically acceptable salt thereof.

15. The method of claim 12, wherein the composition further comprises an antibacterial agent and a nutritive agent, whereby to promote formation and growth of granulation tissue.

16. The method of claim 12, wherein the composition further comprises monosaccharide, whereby to accelerate revascularization, development of granulation tissue, and wound closure.

17. The method of claim 12, wherein the composition further comprises one or more amino acids, whereby to improve healing.

18. A method for treating a wound in a patient, the method comprising steps of:

providing a gel composition comprising a viscous, continuous phase starch hydrolysate mixture having a dispersed phase of a gelatinization agent with a viscosity between 29,000 and 37,000 centipoise; and spreading a therapeutically effective amount of the gel composition on the wound for a sufficient period of time to initiate wound healing.

19. The method of claim 18, wherein the starch hydrolysate mixture has a dextrose equivalent of not more than 30.

20. The method of claim 19, wherein the gel composition further includes ascorbic acid and at least one amino acid, whereby to improve healing.

21. The method of claim 20, further including an antibacterial, nutritive agent to promote forming and growth of granulation tissue, and a starch hydrolysate having a dextrose equivalent between 13 and 17.

22. A gel composition for treating a wound in a patient, the gel composition comprising a continuous phase of starch hydrolysate and sterile water and a dispersed phase of gelatinization agent, said starch hydrolysate having a dextrose equivalent of not more than 30, and having a viscosity between 29,000 and 37,000 centipoise.

23. The gel composition of claim 22, wherein said starch hydrolysate is a maltodextrin having a dextrose equivalent of between about 13 and about 17.

24. The gel composition of claim 22, wherein said gelatinization agent is glycerin.

25. The gel composition of claim 22, wherein said gel composition further comprises ascorbic acid or a pharmaceutically acceptable salt thereof.

26. The gel composition of claim 22, wherein said gel composition further comprises an antibacterial agent and a nutritive agent, whereby to promote formation and growth of granulation tissue.

27. The gel composition of claim 22, wherein said gel composition further comprises a monosaccharide, whereby to accelerate revascularization, development of granulation tissue, and wound closure.

28. The gel composition of claim 22, wherein said gel composition further comprises one or more amino acids, whereby to improve healing.

29. A gel composition for treating a wound in a patient, the gel composition having a continuous phase of starch hydrolysate, sterile water, and a dispersed phase of glycerin and includes ascorbic acid, and an antibacterial agent, nutritive agent, a monosaccharide, and at least one amino acid, whereby to accelerate revascularization, development of granulation tissue, and wound closure, and wherein the composition has a viscosity between 29,000 and 37,000 centipoise.

30. The gel composition of claim 29, wherein the starch hydrolysate is a maltodextrine having a dextrose equivalent of between about 13 and about 17.

* * * * *